United States Patent [19]

Robinson et al.

[11] Patent Number: 4,752,581

[45] Date of Patent: Jun. 21, 1988

[54] NOVEL COMPOUNDS

[75] Inventors: Jeffery H. Robinson, Epsom; Ian Dodd, Dorking, both of England

[73] Assignee: Beecham Group p.l.c., England

[21] Appl. No.: 684,593

[22] Filed: Dec. 21, 1984

[30] Foreign Application Priority Data

Dec. 24, 1983 [GB] United Kingdom ............... 8334498

[51] Int. Cl.⁴ ................. C12N 9/68; C12N 9/48; A61K 37/48
[52] U.S. Cl. .................. 435/217; 435/212; 424/94.63; 424/94.64; 424/94.2
[58] Field of Search ............ 435/212, 188, 214, 215, 435/216, 217; 424/94, 94.2, 94.63, 94.64

[56] References Cited

U.S. PATENT DOCUMENTS

| | | | |
|---|---|---|---|
| 4,082,612 | 4/1978 | Robbins et al. | 435/217 |
| 4,285,932 | 8/1981 | Smith | 435/184 X |
| 4,507,283 | 3/1985 | Smith | 435/217 X |
| 4,545,988 | 10/1985 | Nakayama et al. | 435/217 X |
| 4,600,580 | 7/1986 | Smith | 424/88 X |

FOREIGN PATENT DOCUMENTS 213794 3/1987 European Pat. Off. .

OTHER PUBLICATIONS

Summaria, L. et al., *J. Biol. Chem*, vol. 254, pp. 6811–6814, 1979.
Robbins, K. C. et al., *Biochemistry*, vol. 25, pp. 3603–3611, Jun. 1986.
Jackson et al, Biochem. 1982, 21, 6620–6625.
Summaria et al, J. Biol. Chem. 251, No. 18, 5810–5813 (1976).

*Primary Examiner*—Thomas G. Wiseman
*Assistant Examiner*—Jayme A. Huleatt
*Attorney, Agent, or Firm*—Jacobs & Jacobs

[57] ABSTRACT

A fibrinolytically active hybrid protein which comprises one chain of a 2-chain protease linked to a chain of a different 2-chain protease, or to the same chain of the same protease, at least one of the chains in the hybrid protein being derived from a fibrinolytically active protease, such that the hybrid protein has a catalytic site essential for fibrinolytic activity which is optionally blocked by a removable blocking group.

5 Claims, 1 Drawing Sheet

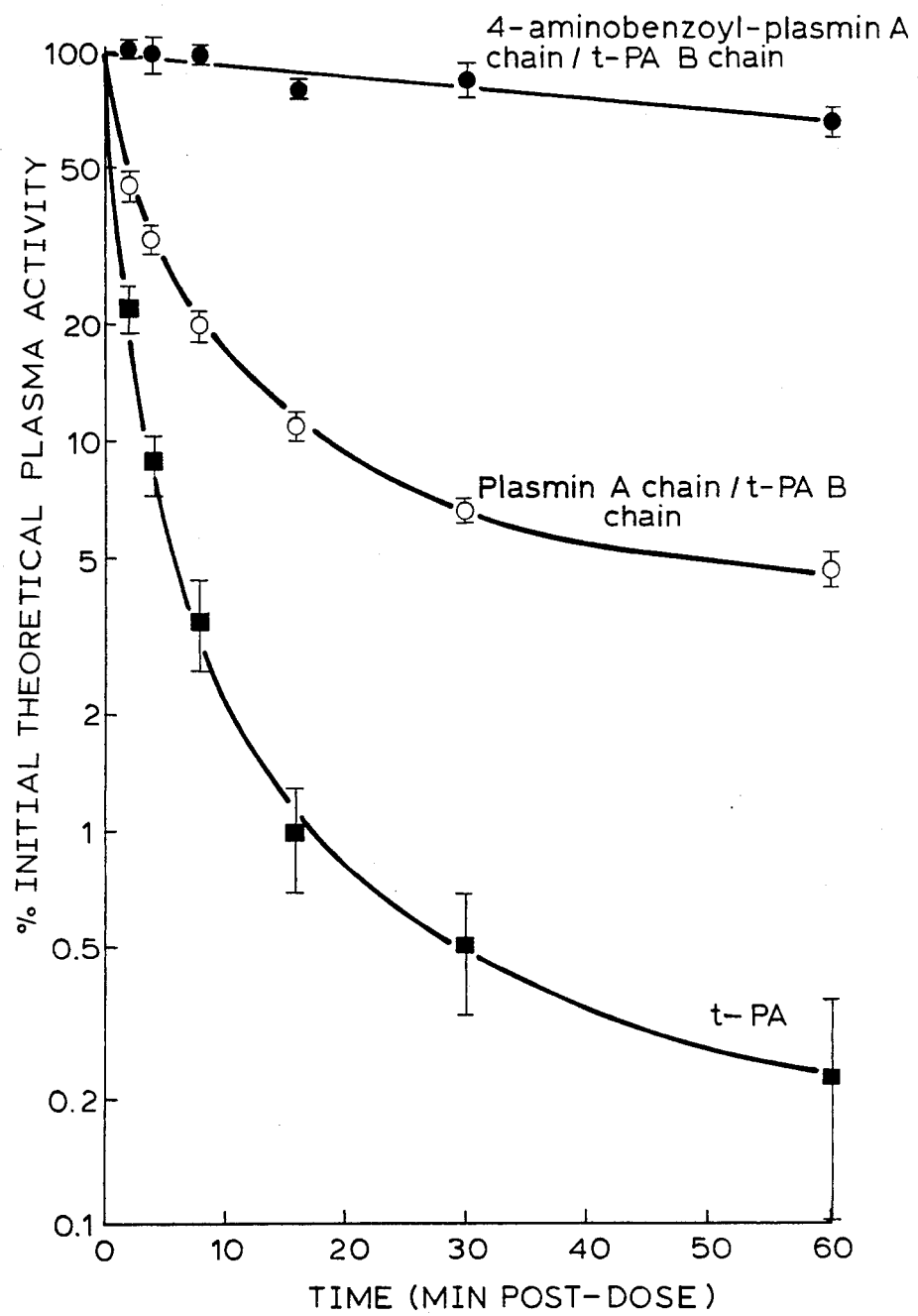

NOVEL COMPOUNDS

The present invention relates to novel hybrid fibrinolytic enzymes, to processes for their preparation and to their use in treating thrombotic diseases.

Human fibrinolytic enzymes may be divided into two general classes; namely, one class that directly digests fibrin, for example, trypsin and plasmin, and a second class that indirectly digests fibrin by activating the inactive zymogen, plasminogen. The latter class, comprising the plasminogen activators, is represented by two major types based on immunological criteria, molecular weight and polypeptide composition (see Collen, D. et al, 1982, Thromb. Haemostas , 48, 294–296). One major type, the urokinase-type plasminogen activators (u-PA) resemble the urinary enzyme urokinase, whereas the other major type, tissue-type plasminogen activators (t-PA) resemble extrinsic activators found in blood, activators extracted from tissues by chaotropic salts and activators secreted by cultured melanoma cells (see Rijken, D. C. and Collen, D., 1981, J. Biol. Chem., 256, 7035–7041; Rijken, D. C. et al, J. Lab. Clin. Med., 97, 477–478). Human plasminogen activators have been used in the treatment of thrombosis. However, the u-PA have the disadvantage that they activate circulating plasminogen as efficiently as fibrin-bound plasminogen and both the u-PA and also the t-PA have the disadvantage that their activity disappears rapidly in vivo due to rapid clearance and inactivation by natural antiproteases.

The above human fibrinolytic enzymes belong to a class of proteases which exist in both a single chain and a 2-chain structure, the two chains being connected by disulphide bridges It has now been found that the desirable properties of two such proteases may be united by forming a single hybrid protein molecule which includes a chain from each of the two proteases.

Accordingly, the present invention provides fibrinolytically active hybrid protein which comprises one chain of a 2-chain protease linked to a chain of a different 2-chain protease, or to the same chain of the same protease, at least one of the chains in the hybrid protein being derived from a fibrinolytically active protease, such that the hybrid protein has a catalytic site essential for fibrinolytic activity which is optionally blocked by a removable blocking group.

The 2-chain protease structure includes an A-chain which has no protease activity and a B-chain with protease activity. Some A-chains, for example those derived from plasmin and t-PA, have a high fibrin affinity. Preferred hybrid proteins of the invention comprise an A-chain of one protease linked to the B-chain of a different protease.

Suitably at least one of the proteases is a serine protease.

As used herein the expression 'removable blocking group' includes groups which are removable by hydrolysis at a rate such that the pseudo-fist order rate constant for hydrolysis is in the range of $10^{-6}$ sec$^{-1}$ to $10^{-3}$ sec$^{-1}$ in isotonic aqueous media at pH 7.4 at 37° C.

Such blocking groups are described in European Pat. No. 0009879 and include acyl groups such as optionally substituted benzoyl or optionally substituted acryloyl.

Suitable optional substituents for benzoyl blocking groups include halogen, $C_{1-6}$ alkyl, $C_{1-6}$ alkoxy, $C_{1-6}$ alkanoyloxy, $C_{1-6}$ alkanoylamino, amino or p-quanidino.

Suitable optional substituents for acryloyl blocking groups include $C_{1-6}$ alkyl, furyl, phenyl or $C_{1-6}$ alkyl-phenyl.

Preferably the optional removable blocking group is 4-aminobenzoyl, N-methylamino benzoyl, N,N-dimethyl-amino benzoyl or 4-methoxybenzoyl.

Examples of hybrid proteins of the invention are (a) plasmin A-chain (PL-A) and tissue plasminogen activator B-chain (t-PA-B)
(b) t-PA A-chain (t-PA-A) and urokinase plasminogen activator B-chain (u-PA-B)
(c) PL-A and u-PA-B
(d) t-PA-A and PL-B
(e) acylated PL-A and t-PA-B Although it is preferred that both of the original proteins which contribute to the hybrid protein of the invention are fibrinolytically active, it is possible for one of them to be fibrinolytically inactive. For example, one of the original proteins may be the fibrinolytically inactive material prothrombin.

The hybrid proteins of the invention may be prepared by mixing a chain of one protease with a chain of another protease, optionally with dialysis, under oxidative conditions.

Preferably, the mixing/dialysis process is carried out for a period of one or more days in the presence of molecular oxygen, and the resulting hybrid protein isolated by chromatographic techniques.

There are various methods known in the prior art that might be beneficially employed to increase the rate of disulphide bond formation; for example, employing —SSO$_3$ derivatives as described in the UK Patent GB No. 2072680 for synthesis of insulin.

Where the hybrid protein contains a blocked catalytic site, the blocking is carried out on either an individual chain or on the formed hybrid protein by methods analogous to those described in European Pat. No. 0009879. The blocking is preferably effected after formation of the hybrid protein.

Alternatively, the hybrid proteins of the invention may be prepared by taking the genetic information (DNA sequence) of each protein, cutting and ligating this to construct a new DNA sequence coding for the hybrid protein, and expressing this DNA in prokaryote or eurokaryote hosts.

The separate protease chains may themselves be prepared by mild reduction of each original protease to break interchain disulphide bridges, followed by separation of the functional chains by affinity chromatography. The separate chains may then be stored for up to several months, preferably at temperatures of from —70° C. to 0° C., until required for use. The hybrid proteins of this invention are preferably administered as a pharmaceutical composition for the treatment of thrombotic diseases.

Accordingly the present invention also provides a pharmaceutical composition comprising a hybrid protein of the invention in combination with a pharmaceutically acceptable carrier.

The compositions according to the invention may be formulated in accordance with routine procedures as pharmaceutical compositions adapted for intravenous administration to human beings.

Typically compositions for intravenous administration are solutions of the sterile hybrid protein in sterile isotonic aqueous buffer. Where necessary the composition may also include a solubilising agent to keep the hybrid protein in solution and a local anaesthetic such as lignocaine to ease pain at the site of injection. Generally, the hybrid protein will be supplied in unit dosage form for example as a dry powder or water free concentrate in a hermetically sealed container such as an ampoule or sachette indicating the quantity of protein in activity units, as well as an indication of the time within which the free protein will be liberated. Where the protein is to be administered by infusion, it will be dispensed with an infusion bottle containing sterile pharmaceutical grade 'Water for Injection'. Where the protein is to be administered by injection, it is dispensed with an ampoule of sterile water for injection. The injectable or infusable composition will be made up by mixing the ingredients prior to administration.

The quantity of material administered will depend upon the amount of fibrinolysis required and the speed with which it is required, the seriousness of the thromboembolic condition and position and size of the clot. The precise dose to be employed and mode of administration must per force in view of the nature of the complaint be decided according to the circumstances by the physician supervising treatment. However, in general, a patient being treated for a mature thrombus will generally receive a daily dose of from 0.01 to 2.0 mg/kg of body weight either by injection in up to five doses or by infusion.

Within the above indicated dosage range, no adverse toxicological effects have been observed with the compounds of the invention.

Accordingly, in a further aspect of the invention there is provided a method of treating thrombotic diseases, which comprises administering to the sufferer an effective non-toxic amount of a hybrid protein of the invention.

The following Examples illustrate the invention.

EXAMPLE 1

Synthesis of lys-plasmin A-chain/t-PA B-chain hybrid

The example may be divided conveniently into four parts:
(a) isolation of the A-chain of plasmin
(b) isolation of the B-chain of t-PA
(c) formation of the plasmin A-chain/t-PA B-chain hybrid
(d) characterisation of the hybrid.

(a) Isolation of the A-chain of plasmin

Essentially salt-free plasminogen (2.0 mg), dissolved at 15 mg/ml in 0.05 M Tris/0.1 M NaCl/25% (v/v) glycerol pH 9.0, was activated by low molecular weight u-PA (Abbott) at 500 CTAu/ml (equivalent to a plasminogen:u-PA molar ratio of 1000:1) for 1h at 27° C. to produce plasmin. Mild reduction of plasmin to its constituent A- and B-chains and their subsequent separation were performed using methods slightly modified from that of Summaria, L. et al (J. Biol. Chem., 1979, 254, 6811). The plasmin and u-PA mixture was treated with leupeptin (15 mg/ml) and dithiothreitol (0.05 M), flushed with $N_2$ and incubated for a further 3h at 6° C. The bulk was then applied to a column ($V_t$ 1.0 ml) of lysine Sepharose* CL4B previously equilibrated with 0.1 M NaH$_2$PO$_4$/0.1 mg/ml leupeptin pH 7.4. The applied sample was washed through with 0.1 M NaH$_2$PO$_4$/0.003 M dithiothreitol pH 7.4 until the baseline had stabilised. The A chain of plasmin was then desorbed from the column using 0.1 M NaH$_2$PO$_4$/0.003 M dithiothreitol/0.5 M ε-aminocaproic acid (EACA) pH 7.4. Chromatography was carried out at 6° C. at 100 ml/h/cm$^2$. All fractions (nominal 1.5 ml) were collected into glycerol (0.5 ml). The eluate from the column was monitored continuously at 280 nm. Protein concentration in the EACA-containing fractions was determined by the method of Bradford (Anal. Biochem., 1976, 72, 248) using bovine serum albumin as standard. The peak fraction contained 320 μg protein/ml. 1 ml of this solution was augmented with 0.05 M Tris, 0.02 M L-lysine and 0.003 M EDTA by addition of 0.05 ml of a 20-fold concentrated stock solution. The pH was noted at 8.5–9.0 using Neutralit* paper (Merck). This solution, containing the A-chain of plasmin, was stored on ice for approx. 2h.

Sepharose is a trade mark
Neutralit is a trademark (b) Isolation of the B-chain of t-PA A preparation of mainly 2-chain t-PA (0.65 mg, as determined by protein analysis) was dissolved at 2 mg/ml in 0.05 M Tris/0.1 M NaCl/25% (v/v) glycerol pH 9.0. Mild reduction was effected by incubating the t-PA solution with dithiothreitol (0.01 M) and leupeptin (2 mg/ml) for 1h at 6° C. in a nitrogen atmosphere. The bulk of the mixture was applied to a column ($V_t$ 2.0 ml) of lysine Sepharose CL4B previously equilibrated with 0.1 NaH$_2$/PO$_4$/0.1 mg/ml leupeptin pH 7.4. The column was washed with 0.1 M NaH$_2$PO$_4$, 0.003 M dithiothreitol pH 7.4 until the baseline had stabilised. All parts of the chromatography were carried out at 6° C. at 100 ml/h/cm$^2$. Fractions (nominal 0.6 ml) were collected into glycerol (0.2 ml). The $V_o$ fractions (containing the unadsorbed material, essentially t-PA B-chain) were assayed for protein content and for amidolytic activity using S-2288 (KabiVitrum). The fractions with the highest amidolytic activity were pooled to give a solution of 2.2 ml containing 165 μg protein and 25,000 SU (where 1 SU=$\Delta OD_{405\ nm}^{1\ cm}$ 0.001 min$^{-1}$ using 1 mM S-2288 in 0.1 M Trien pH 8.0, 0.05% NaN$_3$ containing 0.2 mg/ml soya bean trypsin inhibitor). The pool was augmented with 0.05 M Tris, 0.02 M L-lysine and 0.003 M EDTA by addition of 0.11 ml of a 20-fold concentrated stock solution. The pH was noted at 9.0 (using Neutralit paper) and the pool was then stored on ice for 1h.

(c) Formation of the plasmin A-chain/t-PA B-chain hybrid

The preparation of plasmin A-chain described above (320 μg protein) and the preparation of t-PA B chain described above (160 μg protein) were mixed in a small polystyrene vessel. The mixture was transferred to 8/32" dialysis tubing (Scientific Instrument Centre Ltd.) that had been autoclaved in approx. 0.001 M EDTA and then thoroughly washed with water. The mixture (3.2 ml, 150 μg protein/ml), containing approx. equimolar amounts (5.3 nmoles) of each chain type, was subjected to mild oxidation in the presence of air by dialysis against 30 vol of 25% (v/v) glycerol/0.04 M Tris/0.02 M L-lysine/0.08 M NaCl/0.003 M EDTA pH 9.0 at 6° C. for 3d. The dialysis buffer was stirred. The non-diffusable material was stored at −40° C. for 4d and then was further dialysed for 8d at 6° C. against 40 vol of the same buffer. Aliquots of the nondiffusable material were removed at intervals and were stored at −40° C.

(d) Characterisation of the hybrid

Sodium dodecylsulphate polyacrylamide gel electrophoresis (SDS PAGE) in 8% separating gels using 4% stacking gels but otherwise as described by Laemmli (Nature, 1970, 227, 680) was used to separate the various $M_r$ components of the hybrid-containing solution. Bands of fibrinolytic activity were identified using fibrin zymography, essentially as described by Granelli-Piperno & Reich (J. Exp. Med., 1978, 148, 223). These experiments demonstrate that in the hybrid mixture 15 min after the start of dialysis, thrombolytic activity is present almost entirely in the $M_r=32,000$ region of the zymogram. However, in the samples removed at 24h, 72h and 9d, significant fibrinolytic activity was also present as a doublet at $M_r=88,000$ and 92,000 (hereafter referred to as the 90K doublet). It has also been shown by incorporating specific antibody into a zymogram, that the 90K doublet fibrinolytic activity can be inhibited by anti-t-PA IgG but is not inhibited by a control preparation of anti-u-PA IgG. The possibility that the fibrinolytic activity in the 90K doublet may be due to plasmin contamination of the plasmin A-chain preparation is ruled out by (a) the relative insensitivity of the fibrin layer to lysis by plasmin, (b) the virtual absence of 90K doublet activity in the $t = 15$ min sample and (c) the contrasting 90K doublet activities on the two antibody-containing zymograms.

EXAMPLE 2

Purification and characterisation of hybrid enzyme comprising lys-plasmin A-chain and t-PA B-chain The synthesis of lys-plasmin A/t-PA B hybrid was essentially as described in Example 1 except that:
(a) leupeptin was omitted during the t-PA reduction procedure;
(b) t-PA reduction was for 2h at 5° C.;
(c) the pre-dialysis mixture contained 3 nmoles of each chain type;
(d) the dialysis was carried out against 40 vol dialysis buffer/24h/5° C. followed by a fresh 40 vol dialysis buffer/24h/5° C.

The dialysed retentate (2.4 ml) was diluted with 5 vol 0.02 M phosphate/0.15 M NaCl/0.01% Tween 80, pH 7.4 (PBS/TW) and applied to a column ($V_t$ 2.9 ml) of lysine Sepharose equilibrated with PBS/TW. After application of the dialysed retentate the column was washed with (a) PBS/TW, (b) 0.02 M Tris/0.5 M NaCl/0.01% Tween 80, pH 7.4 and (c) as (b) but additionally containing 0.5 M L-arginine. All parts of the chromatography were carried out at 150 ml/h/cm² at 5° C. Eluate from the column was collected as fractions. Each fraction was assayed using the chromogenic substrate S-2288. The result showed that most of the S-2288 activity was in the fractions that contained the unadsorbed material. The remainder was in the fractions containing the arginine-dissociable material. When analysed by SDS PAGE followed by fibrin zymography it was evident that the unadsorbed material contained only $M_r=$approx. 30,000 plasminogen activator and the arginine-dissociable material contained only an $M_r=$approx. 90,000 plasminogen activator.

The fractions containing the $M_r=90,000$ activator were pooled with similarly produced hybrid preparations, dialysed against solid PEG 20,000 for 2h at 6° C. and the dialysed retentate removed. This solution was then buffer-exchanged into 0.05 M NH₄HCO₃ using Sephadex G-25 and lyophilised. The pre-lyophilisation solution when analysed by SDS PAGE followed by zymography showed a single major band of fibrinolytic activity at $M_r$ approx. 90,000 (which was believed to be a doublet of two species at approx. 88,000 and 92,000) and minor components of approx. 150,000 and approx. 86,000. Assay by fibrin plate or using S-2288 gave a fibrinolytic activity:amidolytic activity (IU:SU) ratio of 0.2 to 0.3 for the preparation as a whole. The dose response of the preparation on fibrin plates was parallel to that of t-PA.

EXAMPLE 3

Synthesis and isolation of hybrid comprising lys-plasmin A-chain and u-PA B-chain (a) Isolation of the A-chain of plasmin The isolation of lys-plasmin A-chain was similar to that described in Example 1 except that:
(a) incubation with dithiothreitol was for 3.5h at 5° C.;
(b) lysine Sepharose bed volume was 1.5 ml.

The peak ε-aminocaproic acid (EACA)-containing fraction (1.7 ml) was augmented with 0.05 M Tris, 0.02 M L-lysine and 0.003 M EDTA by addition of a 20-fold concentrated stock solution. The solution was adjusted to pH 9.0 using NaOH. 0.1 ml of this solution was stored at $-40°$ C. for approx. 3 months (=solution A).

The second peak-EACA-containing fraction (ca. 1.7 ml) was stored untreated at $-40°$ C. for approx. 3 months. It was then thawed, and was augmented with Tris/lys/EDTA mixture as described above, to give solution B. Solution A was then thawed and mixed with solution B to give solution C. The total volume of this solution was 1.78 ml and the pH was recorded at pH 8.5-9.0 using Neutralit paper. Protein content was 121 μg protein/ml. Solution C was held on ice until required.

(b) Isolation of urokinase-type plasminogen activator (u-PA) B-chain $1 \times 500,000$ IU (5 mg) u-PA (Serono) was dissolved at 20 mg/ml in deionised H₂O. 0.095 ml, equivalent to 2 mg, was transferred to a polypropylene microtube (Sarstedt), mixed with an equal volume of 0.02 M 2-mercaptoethanol/0.1 M Tris-HCl/0.3 M NaOH/0.04 M EDTA pH 8.0 and incubated at 21° to 24° C. for 17h. The sample was then mixed with 0.02 ml of a reduced u-PA solution of similar composition that had been prepared 3d previously. 0.2 ml from this mixture was diluted 10-fold using 1.8 ml 0.02 M Tris/0.003 M 2-mercaptoethanol pH 7.4 and was applied to a column ($V_t$ approx. 4 ml) of p-aminobenzamidine Sepharose (Pierce) that had been equilibrated with 0.02 M Tris/0.003 M 2-mercaptoethanol pH 7.4. After application of the reduced u-PA solution the column was washed with (a) equilibration buffer, (b) 0.02 M Tris/0.5 M NaCl/25% (v/v) glycerol/0.003 M 2-mercaptoethanol pH 7.4 and (c) as (b) but additionally containing 0.5 M L-arginine.

The peak arginine-containing fractions (vol. 4.9 ml) were augmented with 0.05 M Tris/0.02 M L-lysine/0.003 M EDTA by addition of 0.245 ml of a 20-fold-concentrated stock solution. The pH was noted at 8.5. Protein content was 82 μg/ml. This solution was regarded as "the u-PA B-chain pool".

(c) Synthesis of the plasmin A/u-PA B hybrid u-PA B-chain pool (1.3 ml of above solution) and lysplasmin A-chain pool (1.76 ml of solution C of plasmin A pool) were mixed to give an equimolar (nominal 3.6 nmole) solution of u-PA B and plasmin A of total volume 3.06 ml. This solution was transferred to Medicell visking tubing and dialysed against 0.05 M Tris/0.02 M L-lysine/0.08 M NaCl/0.003 M EDTA/25% (v/v) glycerol pH 9 (30 vol/24h) followed by fresh dialysate (30 vol/3d). All dialysis was carried out at 5° C. in the presence of air (atmospheric). The dialysed retentate present at 4d was transferred to a polystyrene bijou and stored at −40° C.

(d) Characterisation and purification of product

SDS PAGE followed by fibrin zymography, both as described in Example 1, were carried out on all samples taken throughout the dialysis procedure. These showed that a fibrinolytic enzyme with $M_r$ approx. 90,000 was formed during the 0–24h dialysis period with little change in yield thereafter. The bulk dialysed retentate (3.7 ml) was diluted with 9 vol 0.02 M phsphate/0.15 M NaCl/0.01% Tween 80, pH 7.4 and applied directly to a column ($V_t$ 1.8 ml) of lysine Sepharose equilibrated in the dilution buffer. After the dialysed retentate had been applied, the column was washed sequentially with (a) equilibration buffer and (b) as (a) but additionally containing 0.5 M ε-aminocaproic acid (EACA). All parts of the chromatography were at 50 ml/h/cm² at 5° C. The peak EACA-containing fractions were buffer-exchanged into 0.05 M NH$_4$HCO$_3$ and were lyophilised. The lyophilisate was reconstituted in deionised H$_2$O. This solution contained 360 CTA units plasminogen activator, as determined on fibrin plates. By SDS PAGE followed by fibrin zymography the preparation contained a single fibrinolytically active component, at $M_r$=approx. 90,000, which was identical in $M_r$ to the plasmin A/t-PA B hybrid.

EXAMPLE 4

Preparation, isolation and characterisation of 4-aminobenzoyl (plasmin A)/t-PA B The method for reversible active site-acylation of the hybrid plasmin A/t-PA B was essentially as described previously (Smith, R. A. G., European Pat. No. 0009879).

Briefly, salt-free, lyophilised lys-plasmin A/t-PA B (15,000 IU) was dissolved in 0.1 M phosphate pH 7.4 (2.1 ml) and incubated at 26° C. with 1 mM 4′-amidinophenyl p-aminobenzoic acid (APAB) by addition of 0.042 ml APAB (50 mM in Dimethylsulphoxide). Assay of the incubate at t=30 min indicated that 99.6% of the original amidolytic activity had been inhibited. At t=40 min the solution was buffer-exchanged, using Sephadex G-25 at 5° C., into 0.02 M phosphate/0.15 M NaCl/0.01% Tween 80 pH 7.4 (3.0 ml) to remove excess acylating reagent; the product was stored at −70° C.

The product was shown to have a deacylation half-life of approximately 88 min and a deacylation rate constant of approximately $1.37 \times 10^{-4}$ sec$^{-1}$. The IU:SU ratio of deacylated hybrid was 0.27, which was the same (within experimental error) as the original hybrid preparation before acylation.

EXAMPLE 4A

Preparation of N-methyl-aminobenzoyl (plasmin A)/t-PA B and N,N-dimethyl-aminobenzoyl (plasmin A)/t-PA B The two title hybrid proteins were prepared by methods analogous to those described in Example 4.

EXAMPLE 5

Synthesis, isolation and characterisation of t-PA A-chain/u-PA u-PA B-chain hybrid (a) Isolation of u-PA B-chain Urokinase-type plasminogen activator (Serono, 10 mg) was mildly reduced essentially as described in Example 3 except that the 2-mercaptoethanol concentration during the reduction period was 0.02 M and the incubation period was 24h. The mildly reduced u-PA preparation (1.0 ml) was then mixed with 0.02 M.Tris/0.0011 M 2-mercaptoethanol pH 7.4 (9 ml) (to give a final 2-mercaptoethanol concentration of 0.003 M) and then chromatographed on p-aminobenzamidine Sepharose as described in Example 3. The peak argininedissociable fractions, which had been collected into glycerol (to give a final glycerol concentration of 44% (v/v)), primarily contained u-PA B-chain. These fractions were pooled and stored at −40° C. for 7d until used.

(b) Isolation of t-PA A-chain

Two-chain t-PA (480,000 SU) at 210,000 SU/ml in 0.05 M Tris/0 1 M NaCl/25% (v/v) glycerol pH 9 was treated with dithiothreitol (10 mM), flushed with nitrogen and incubated for 2h at 5° C. The incubate was then applied to a lysine Sepharose column ($V_t$ 8.6 ml) equilibrated with 0.1 M NaH$_2$PO$_4$/0.1 mg/ml leupeptin pH 7.4. After application of the incubate, the column was washed with (a) 0.1 M NaH$_2$PO$_4$/0.003 M dithiothreitol pH 7.4 and (b) as (a) but additionally containing 0.5 M ε-aminocaproic acid (EACA). The eluate of buffer (b) was collected into glycerol to give a final glycerol concentration of approx. 25% (v/v). All elutions were carried out at about 100 ml/h/cm². The peak EACA fractions were believed to contain t-PA A-chain and were pooled and stored at −40° C. for approx. 40d. The A-chain pool was then buffer-exchanged into 0.02 M phosphate/0.3 M NaCl/0.003 M dithiothreitol/0.01% Tween 80 pH 7.4 using a column of Sephadex G-25. The fractions of the Sephadex column containing the A chain were concentrated by dialysis against PEG 20,000. Further purification of the A-chain was carried out by chromatographing the preparation on pABA-Sepharose ($V_t$ 2.4 ml) equilibrated in the buffer used in the Sephadex G-25 column. The applied material was washed through with equilibration buffer, followed by 0.1 M phosphate/0.5 M EACA/0.003 M dithiothreitol, pH 7.4. The fractions containing the unadsorbed solution were concentrated by dialysis against PEG 20,000 to give a solution of 5.6 ml containing 80 μg protein/ml.

(c) Synthesis, isolation and characterisation of t-PA A/u-PA B hybrid

The u-PA B-chain pool (11.2 ml) was augmented with 0.05 M Tris, 0.02 M L-lysine and 0.003 M EDTA by addition of 0.56 ml of a 20-fold concentrated stock solution, and was held on ice. The t-PA A-chain pool (5.6 ml) was similarly augumented using 0.28 ml of the 20-fold concentrated stock solution. The u-PA B-chain pool and the t-PA A-chain pool were then mixed and were transferred to dialysis tubing. The mixture was dialysed against 40 vol 0.04 M Tris/0.02 M l-lysine/0.08 M NaCl/0.003 M EDTA/25% (v/v) glycerol pH 9.0 for 24h at 5° C. followed by fresh buffer (40 vol) for 5d at 5° C.

The dialysed retentate was removed from the dialysis bag on day 6, diluted with 4 vol 0.02 M phosphate/0.15 M NaCl/0.01% Tween 80 pH 7.4 (PBS/TW) and applied directly to a column of lysine Sepharose that had been equilibrated in PBS/TW. The applied hybrid solution was washed through with PBS/TW. The column was then washed with (a) 0.02 M Tris/0.5 M NaCl/0.01% Tween 80 pH 7.4 and (b) as (a) but additionally containing 0.5 M arginine. Eluate from the column was collected in fractions. On the basis of an assay using S-2288 two fractions that contained L-arginine-dissociable amidolytic activity were pooled. This final pool was believed to contain the t-PA A-chain/u-PA B-chain hybrid. When analysed by SDS PAGE and fibrin zymography, as described in Example 1, the pool was shown to contain five plasminogen activators, at $M_r$=approx. 40,000, 47,000, 56,000, 65,000 and 90,000. By incorporating specific antibody into other fibrin zymograms it was demonstrated that the $M_r$=approx. 40,000, 56,000 and 65,000 species could be neutralised by both anti-t-PA IgG and anti-u-PA IgG. These species are believed to be t-PA A/u-PA B hybrids. The occurrence of hybrids of three $M_r$ is due to the use originally of partially degraded t-PA in which the t-PA A-chain is present in multiple forms (e.g. Banyai, L. et al, 1983, FEBS Lett., 163, 37–41).

EXAMPLE 6

(a) Methods

Assay of fibrinolytic activity in the bloodstream of guinea pigs

Male Dunkin Hartley guinea pigs (350–450 g) were anaesthetized with urethane (25% w/v solution; 6 ml/kg i.p.). One carotid artery was cannulated for collection of blood samples. One femoral vein was cannulated for injection of heparin (50 U/kg i.v.) and compound under test. Approximately 5 min after heparinization, a pre-dose blood sample (2 ml) was taken and mixed with 0.1 volumes 129 mM trisodium citrate. The compound under test was then injected (1 ml/kg) over 10s. Further blood samples were taken exactly 2, 4, 8, 16, 30 and 60 min later. Heparin treatment (50 U/kg i.v.) was repeated after the 30 min sample to maintain cannula patency. All citrated blood samples were kept on ice until the end of each experiment, then centrifuged at 1700 g for 15 min at 4° C. to obtain plasma. The euglobulin fraction was precipitated by adding 0.1 ml of each plasma to 1.82 ml ice-cold 0.011% (v/v) acetic acid in water. After 30 min standing in ice, all tubes were centrifuged at 1700 g for 15 min at 4° C. The supernatants were poured away, the inner walls of each tube carefully wiped dry and each precipitate redissolved in 0.4 ml phosphate-buffered saline, pH 7.4, containing 0.01% (v/v) Tween 80. Aliquots (30 μl) were then applied to fibrin plates in quadruplicate. Fibrin plates were prepared from 0.4% (w/v) human fibrinogen (Kabi, Grade L, Flow Laboratories, Scotland) dissolved in 0.029 M barbitone in 125 mM NaCl, pH 7.4, pipetted (10 ml) into 10×10 cm square plastic dishes (Sterilin) and clotted by rapid mixing with 0.3 ml bovine thrombin (50 NIH units/ml, Parke-Davis, U.K.). Plates were incubated at 37° C. for 18–24h usually, but longer if required, and stained with aqueous bromophenol blue. For each lysis zone, two diameters perpendicular to each other were measured using Vernier callipers. All diameters for each sample were averaged, and this mean converted to fibrinolytic activity by reference to a calibration curve. The latter was obtained by adding known amounts of the compound under test to the pre-dose plasma of each animal. These standards were processed using the same methods and at the same time as the experimental samples. To construct the calibration curve, diameters (mm) were plotted against $log_{10}$ concentration of compound. The plasma concentration of compound in each experimental sample was expressed as a percentage of that expected on the assumption of 50 ml plasma/kg body weight for each guinea pig.

(b) Results

FIG. 1 shows the clearance from guinea pig bloodstream of t-PA, the plasmin A-chain/t-PA B-chain hybrid and an acylated derivative (4-aminobenzoyl) of the hybrid.

Thrombolysis in vivo is generally considered to be a prolonged event which requires significant concentrations of activator to be present over a long period. In the case of t-PA, its activity disappears very quickly whereas activity of the hybrid is significantly prolonged in the bloodstream. A further improvement in pharmacokinetics is seen in the 4-aminobenzoyl derivative of the hybrid protein (half-life of acylated hybrid approx. 106 min as compared to rapid phase of clearance of t-PA with half-life of approx. 2 min).

We claim:

1. A fibrinolytically active hybrid protein, which comprises plasmin A-chain covalently linked to tissue plasminogen activator B-chain and which has a catalytic site essential for catalytic activity.

2. A fibrinolytically active hybrid protein, which comprises plasmin A-chain covalently linked to tissue plasminogen activator B-chain and which has a catalytic site essential for catalytic activity blocked by a removable blocking group.

3. The hybrid protein according to claim 2, wherein said removable blocking group is benzoly on benzoyl derivatives.

4. The hybrid protein according to claim 1 wherein the benzoyl derivatives are substituted by substituents selected from the group consisting of halogen, $C_{1-6}$ alkyl, $C_{1-6}$ alkoxy, $C_{1-6}$ alkanoyloxy, $C_{1-6}$ alkanoylamino, amino and p-guanido.

5. The hybrid protein according to claim 3 selected from the group consisting of 4-Aminobenzoyl (plasmin A-chain) covalently linked to tissue plasminogen activator B-chain, N-methylaminobenzoyl (plasmin A-chain) covalently linked to tissue plasminogen activator B-chain and N,N-dimethylaminobenzyl (plasmin A-chain) covalently linked to tissue plasminogen activator B-chain.

* * * * *

UNITED STATES PATENT AND TRADEMARK OFFICE
CERTIFICATE OF CORRECTION

PATENT NO. : 4,752,581
DATED : June 21, 1988
INVENTOR(S) : Jeffery Hugh Robinson et al It is certified that error appears in the above-identified patent and that said Letters Patent is hereby corrected as shown below:

Claim 3, line 2, "benzoly on" should read --benzoyl or--.

Claim 4, line 1, "1" should read --3--.

Claim 5 should read as follows:
--5. The hybrid protein according to claim 3 selected from the group consisting of 4-aminobenzoyl (plasmin A-chain covalently linked to tissue plasminogen activator B-chain);

N-methylaminobenzoyl (plasmin A-chain covalently linked to tissue plasminogen activator B-chain); and N,N-dimethylaminobenzoyl (plasmin A-chain covalently linked to tissue plasminogen activator B-chain).

Signed and Sealed this

Twenty-sixth Day of September, 1989

Attest:

DONALD J. QUIGG

Attesting Officer

Commissioner of Patents and Trademarks